United States Patent [19]

Fischer

[11] 3,989,508
[45] Nov. 2, 1976

[54] SUBSTITUTED NITROANILINES AND UREAS AS HERBICIDAL MIXTURES

[75] Inventor: Adolf Fischer, Mutterstadt, Germany

[73] Assignee: BASF Aktiengesellschaft, Ludwigshafen (Rhine), Germany

[22] Filed: May 9, 1974

[21] Appl. No.: 468,372

Related U.S. Application Data

[60] Continuation-in-part of Ser. No. 297,270, Oct. 13, 1972, abandoned, which is a division of Ser. No. 162,317, July 13, 1971, Pat. No. 3,849,107.

[30] Foreign Application Priority Data

Jan. 28, 1970 Germany.............................. 2037265

[52] U.S. Cl.................................... 71/120; 71/90; 71/94; 71/103; 71/105; 71/106; 71/119; 71/121
[51] Int. Cl.²......................................... A01N 9/20
[58] Field of Search ................. 71/121, 120, 63, 88

[56] References Cited

UNITED STATES PATENTS

| | | | |
|---|---|---|---|
| 2,726,150 | 12/1955 | Wolter................................. | 71/120 |
| 3,112,342 | 11/1963 | Luckenbaugh ....................... | 71/120 |
| 3,373,010 | 3/1968 | Olson.................................... | 71/121 |
| 3,385,690 | 5/1968 | Luckenbaugh ....................... | 71/120 |
| 3,849,107 | 11/1974 | Fischer ................................. | 71/121 |

FOREIGN PATENTS OR APPLICATIONS

| | | | |
|---|---|---|---|
| 1,643,719 | 1/1971 | Germany ............................. | 71/121 |

*Primary Examiner*—Glennon H. Hollrah
*Attorney, Agent, or Firm*—Johnston, Keil, Thompson & Shurtleff

[57] ABSTRACT

Herbicidal mixtures useful as selective herbicides embodying 2,4,6-trisubstituted anilines, at least one substituent being nitro, and substituted ureas in a weight ratio of 1:3 to 3:1.

7 Claims, No Drawings

SUBSTITUTED NITROANILINES AND UREAS AS HERBICIDAL MIXTURES

RELATED APPLICATION

This application is a continuation-in-part of my copending application Ser. No. 297,270, filed 10/13/72, now abandoned which is a division of my application Ser. No. 162,317, filed July 13, 1971, now U.S. Pat. No. 3,849,107.

The present invention relates to herbicides, particularly selective herbicides, which are suitable for controlling the growth of unwanted plants in crop plants.

It is known to use substituted dinitroaniline derivatives, phosphoric acids, pyridazones, substitutedureas, triazines and biscarbamates as herbicidal active ingredients. However, their action is not always satisfactory.

I have now found that herbicides comprising a mixture of a. a compound of the formula

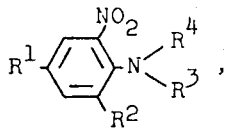

where $R^1$ denotes hydrogen, nitro, alkyl, trifluoromethyl or methylsulfonyl, $R^2$ denotes nitro, alkyl, trifluoromethyl or methylsulfonyl, $R^3$ and $R^4$ are identical or different and denote hydrogen, a linear or branched, saturated or unsaturated aliphatic radical which may be substituted by halogen, cyano, alkoxy or azido, or haloacetyloxyalkyl or alkylcarbamoyloxyalkyl, and $R^3$ and $R^4$, together with the nitrogen atom whose substituents they are, may also form a hexamethylenimine ring, with b. a compound of the formula

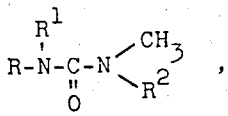

where R denotes phenyl which may be substituted by halogen, nitro, alkyl, alkoxy, alkenoxy, alkynoxy, haloalkyl, alkyl or dialkylcarbamoyloxy, a cycloaliphatic, bicycloaliphatic or tricycloaliphatic radical which may be substituted by halogen or alkyl, 3-benzothiazoly substituted or unsubstituted phenoxyalkyl, alkenyl or alkynylcarbamoyoxy, $R^1$ denotes hydrogen, cyclooctenyl or cyclohexenyl, $R^2$ denotes hydrogen, alkyl, alkoxy, alkoxyalkyl, isobuten-(1)-yl-3, α,α-dimethylpropargyl, cyanoalkyl, or carboxyalkyloxy, $R^2$ further denotes an alkyl

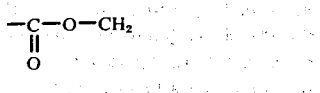

radical or its salts or esters, have a good herbicidal action, both pre- and postemergence, on weeds such as Chenopodium album, Galinsoga parviflora, Sinapis arvensis, Polygonum spp., Amaranthus spp., and Portulaca oleracea; on grassy weeds such as Poa spp., Bromus spp., Avena sativa and Cyperus spp.; and on millet types such as Panicum spp., Setaria spp., Digitaria spp., and Echinochloa spp. in the following crops: Gossypium spp., Soja hispida, Brassica napus, Beta spp., and Oryza sativa.

The individual active ingredients may be mixed together in any desired ratio; however, mixtures in which the ratio by weight of a to b compounds above is from 3:1 to 1:3 are preferred.

The agents according to the invention may be used as solvents, emulsions, suspensions or dusts. The form of application depends entirely on the purpose for which the agents are being used; in any case it should ensure a fine distribution of the active ingredient.

For the preparation of solutions to be sprayed direct, hydrocarbons having boiling points higher than 150° C, e.g. tetrahydronaphthalene or alkylated naphthalenes, or organic liquids having boiling points higher than 150° C and having one or more than one functional group, e.g. the keto group, the ether group, the ester group or the amide group, this group or these groups being attached as substituent(s) to a hydrocarbon chain or being a component of a heterocyclic ring, may be used as spray liquids.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e.g. polyethylene oxide adducts. Concentrates which are suitable for dilution with water may be prepared from active ingredient, emulsifying or dispersing agent and possibly solvent.

Dusts may be prepared by mixing or grinding the active ingredients with a solid carrier, e.g. kieselguhr, talc, clay or fertilizers.

To improve the action, wetting agents and adhering agents or oils may also be added.

EXAMPLE 1

An agricultural plot was sown with Gossupium hirsutum, Setaria viridis, Echinochloa crus-galli, Bromus tectorum, Amaranthus retroflexus and Portulaca oleracea and subsequently treated with the following amounts of the following individual active ingredients and mixtures of them, each active ingredient and each mixture being emulsified or dispersed in 500 liters of water per hectare:

I N-allyl-N-β-chloroethyl-2,6-dinitro-4-trifluoromethylaniline, 1.5 and 4 kg per hectare;
II N-propyl-N-β-chloroethyl-2,6-dinitro-4-trifluoromethylaniline, 1 and 4 kg per hectare;
III N-propyl-N-β-cyanoethyl-2,6-dinitro-4-trifluoromethylaniline, 2 and 4 kg per hectare;
IV N-ethyl-N-β-chloroethyl-2,6-dinitro-4-trifluoromethylaniline, 2 and 3 kg per hectare;
V N,N-dipropyl-2,6-dinitro-4-methylsulfonylaniline, 1.5 and 3 kg per hectare;
VI N-m-trifluoromethylphenyl-N-1-cyclohex-1-enyl-N',N-40-dimethylurea, 2.5 and 4 kg per hectare;
VII N-m-chlorophenyl-N-1-cyclohex-1-enyl-N',N-40-dimethylurea, 3 and 4 kg per hectare;
VIII N-p-fluorophenyl-N-1-cyclohex-1-enyl-N-methylurea, 2 and 4 kg per hectare;
IX N-m-trifluoromethylphenyl-N',N'-dimethylurea, 1.5 and 3 kg per hectare;
X N-p-chlorophenyl-N',N'-dimethylurea, 1 and 3 kg per hectare;

I + VI : 1.5 + 2.5 kg per hectare;
II + VII : 1 + 3 kg per hectare;
III + VIII: 2 + 2 kg per hectare;
IV + X : 2 + 1 kg per hectare;
V + IX : 1.5 + 1.5 kg per hectare.

After 4 to 5 weeks it was ascertained that the mixtures had a stronger herbicidal action than the individual active ingredients, combined with more favorable crop plant compatibilty.

The results of the experiment are given in the following table:

N-propyl-N-β-azidoethyl-2,6-dinitro-4-trifluoromethylaniline;
N-propyl-N-β-(chloroacetyloxy)-ethyl-2,6-dinitro-4-trifluoromethylaniline;
N,N-bis-(β-chloroacetyloxy)-ethyl-2,6-dinitro-4-trifluoromethylaniline;
N-(β-chloroacetyloxy)-ethyl-2,6-dinitro-4-trifluoromethylaniline;
N-(β-methylcarbamoyloxy)-ethyl-2,6-dinitro-4-trifluoromethylaniline;
N-ethyl-N-β-bromoethyl-2,6-dinitro-4-trifluorome- Table

| kg/ha | I 1.5 | I 4 | II 1 | II 4 | III 2 | III 4 | IV 2 | IV 3 | V 1.5 | V 3 | VI 2.5 | VI 4 | VII 3 | VII 4 | VIII 2 | VIII 4 | IX 1.5 | IX 3 | X 1 | X 3 |
|---|---|---|---|---|---|---|---|---|---|---|---|---|---|---|---|---|---|---|---|---|
| Gossypium hirsutum | 0 | 15 | 0 | 30 | 0 | 20 | 0 | 20 | 0 | 15 | 0 | 35 | 0 | 10 | 0 | 30 | 0 | 20 | 0 | 30 |
| Setaria viridis | 90 | 100 | 55 | 100 | 60 | 95 | 80 | 100 | 80 | 100 | 80 | 100 | 70 | 90 | 70 | 100 | 60 | 95 | 70 | 100 |
| Echinochloa crus-galli | 80 | 60 | 55 | 100 | 60 | 95 | 80 | 100 | 80 | 100 | 95 | 100 | 70 | 90 | 80 | 100 | 60 | 95 | 70 | 100 |
| Bromus tectorum | 80 | 100 | 50 | 100 | 70 | 80 | 60 | 75 | 70 | 95 | 70 | 100 | 70 | 95 | 70 | 100 | 75 | 90 | 60 | 100 |
| Amaranthus retroflexus | 80 | 60 | 25 | 80 | 20 | 50 | 25 | 40 | 20 | 45 | 90 | 100 | 80 | 100 | 80 | 100 | 70 | 100 | 80 | 100 |
| Portulaca oleracea | 30 | 80 | 25 | 75 | 35 | 55 | 30 | 50 | 30 | 60 | 100 | 100 | 80 | 100 | 80 | 100 | 80 | 100 | 80 | 100 |

| kg/ha | I + VI 1.5 + 2.5 | II + VII 1 + 3 | III + VIII 2 + 2 | IV + X 2 + 1 | V + IX 1.5 + 1.5 |
|---|---|---|---|---|---|
| Gossypium hirsutum | 0 | 0 | 0 | 0 | 0 |
| Setaria viridis | 100 | 100 | 100 | 100 | 100 |
| Echinochloa crus-galli | 100 | 100 | 100 | 100 | 100 |
| Bromus tectorum | 100 | 100 | 100 | 100 | 100 |
| Amaranthus retroflexus | 100 | 100 | 100 | 100 | 100 |
| Portulaca oleracea | 100 | 100 | 100 | 100 | 100 |

0 = no damage
100 = complete destruction

The action of the following mixtures corresponds to that of the mixtures in Example 1:

N,N-dipropyl-2,6-dinitro-4-trifluoromethylaniline;
N-β-methoxyethyl-N-β-chloroethyl-2,6-dinitro-4-trifluoromethylaniline;
N-β-methoxyethyl-N-β-azidoethyl-2,6-dinitro-4-trifluoromethylaniline;
N-ethyl-N-butyl-2,6-dinitro-4-trifluoromethylaniline;
N-isobutyl-N-β-cyanoethyl-2,6-dinitro-4-trifluoromethylaniline;
N-ethyl-N-β-cyanoethyl-2,6-dinitro-4-trifluoromethylaniline;
N-methyl-N-β-cyanoethyl-2,6-dinitro-4-trifluoromethylaniline;
N-butyl-N-β-cyanoethyl-2,6-dinitro-4-trifluoromethylaniline;
N-β-methyoxyethyl-N-β-cyanoethyl-2,6-dinitro-4-trifluoromethylaniline;
N-methyl-N-β-cyanoethyl-2,6-dinitro-4-trifluoromethylaniline;
N-butyl-N-β-chloropropyl-2,6-dinitro-4-trifluoromethylaniline;
N-butyl-N-β-chloropropyl-2,6-dinitro-4-trifluoromethylaniline;
N-propyl-N-β-chloropropyl-2,6-dinitro-4-trifluoromethylaniline;
N-propyl-N-β-bromoethyl-2,6-dinitro-4-trifluoromethylaniline;
N,N-bis-β-(chloroethyl)-2,6-dinitro-4-trifluoromethylaniline;
N,N-bis-β-(chloroethyl)-2,6-dinitro-4-methylaniline;
N-propyl-N-allyl-4,6-dinitro-2-trifluoromethylaniline;
N-ethyl-N-βazidoethyl-2,6-dinitro-4-trifluoromethylaniline;
thylaniline;
N-β-methoxyethyl-N-β-bromoethyl-2,6-dinitro-4-trifluoromethylaniline;
N-δ-chloropropyl-N-β-chloroethyl-2,6-dinitro-4-trifluoromethylaniline;
N-propen-(1)-yl-(3)-N-β-chloroethyl-2,6-dinitro-4-methylaniline;
N-propyl-N-β-chloroethyl-2,6-dinitro-4-methylaniline;
N-propyl-N-β-azidoethyl-2,6-dinitro-4-methylaniline;
N-propyl-N-β-azidoethyl-2,6-dinitro-4-methylsulfonylaniline;
N-propyl-N-β-bromoethyl-2,6-dinitro-4-methylsulfonylaniline;
N-propyl-N-β-(chloroacetyloxy)-ethyl-2,6-dinitro-4-methylaniline;
N-propyl-N-β-(chloroacetyloxy)-propyl-2,6-dinitro-4-trifluoromethylaniline; or
N-propyl-N-β-(methylcarbamoyloxy)-propyl-2,6-dinitro-4-trifluoromethylaniline; with
N-m-trifluoromethylphenyl-N-cyclohex-1-enyl-N'-methylurea;
N-3-chlorophenyl-N-cyclohex-1-enyl-N'-methylurea;
N-3-chloro-4-methoxyphenyl-N-cyclohex-1-enyl-N'-methylurea;
N-4-chlorophenyl-N-cyclohex-1-enyl-N'-methylurea;
N-phenyl-N-cyclohex-1-enyl-N'-methylurea;
N-phenyl-N-cyclohex-1-enyl-N'N'-dimethylurea;
1-(m-tert-butylcarbamoyloxyphenyl)-3-methylurea;
1-(m-ethylcarbamoyloxyphenyl)-3-methylurea;
1-(m-allyl-tert-butylcarbamoyloxyphenyl)-3,3-dimethylurea;
1-(m-α,α-dimethylpropyn-(1)-yl-(3)carbamoyloxyphenyl)-3-methyl-3-methoxyurea;
1-(m-α-methyl-α-ethylpropyn-(1)-yl-(3)carbamoyloxyphenyl)-3-methyl-3-methoxyurea;

1-(m-tert-butylallylcarbamoyloxyphenyl)-3-methyl-3-methoxyurea;
N-m-trifluoromethylphenyl-N'-butyn-(1)-yl-(3)-urea;
N-3-chloro-4-methoxyphenyl-N'-methyl-N'-methoxyurea;
N-m-trifluoromethylphenyl-N-methoxymethyl-N'-methylurea;
N-m-trifluoromethylphenyl-N-methoxymethyl-N'-methyl-N'-methoxyurea;
N-m-trifluoromethylphenyl-N-acetyloxymethyl-N',N'-dimethylurea;
N-4-bromophenyl-N-cyclohex-1-enyl-N'N'-dimethylurea;
N-3,4-dichlorophenyl-N-cyclohex-1-enyl-N'N'-dimethylurea;
N-3-chloro-4-methoxyphenyl-N-cyclohex-1-enyl-N'N'-dimethylurea;
N-[1- or 2-(3a, 4, 5, 6, 7,7a-hexahydro)-4-methanoindanyl]-N'N'-dimethyl-N-cyclohex-1-enylurea;
N-m-trifluoromethylphenyl-N-cyclooct-1-enyl-N'N'-dimethylurea;
N-m-trifluoromethylphenyl-N-cyclooctyl-1-enyl-N'-methylurea;
N- 5-(3a,4,5,6,7,7a-hexahydro-4-methanoindanyl-N'N'-dimethylurea;
N- 1- or 2-(3a,4,5,6,7,7a-hexahydro)-4-methanoindanyl-N'N'-dimethylurea;
N-bicyclo-(3,3,0)-octyl-N'N'-dimethylurea;
N-3,4-dichlorophenyl-N'N'-dimethylurea;
N-cyclooctyl-N'N'-dimethylurea; or
N-m-dimethylcarbamoyloxyphenyl-N'-methylurea.

EXAMPLE 2

An agricultural area was sown with *Soja hispida, Digitaria sanguinalis, Bromus tectorum, Amaranthus retroflexus* and *Portulaca oleracea* and subsequently treated with the following amounts of the following individual active ingredients and mixtures of them, each active ingredient and each mixture being dispersed or emulsified in 500 liters of water per hectare:

I   N-allyl-N-β-chloroethyl-2,6-dinitro-4-trifluoromethylaniline, 1 and 3 kg per hectare;
II   N-propyl-N-β-chloroethyl-2,6-dinitro-4-trifluoromethylaniline, 1 and 2 kg per hectare;
III   N',N-dipropyl-2,6-dinitro-4-trifluoromethylaniline, 1 and 3 kg per hectare;
IV   1-m-trifluoromethyl-4-dimethylamino-5-chloropyridazone-6, 2 and 3 kg per hectare;
V   1-phenyl-4,5-dimethoxypyridazone-6, 1 and 2 kg per hectare;
VI   1-m-methylphenyl-4-methoxy-5-bromopyridazone-6, 2 and 3 kg per hectare;
VII   N-m-trifluoromethylphenyl-N-cyclohex-1-enyl-N',N'-dimethylurea; 2 and 3 kg per hectare;
VIII   N,N-dimethyl-N'-[N''-methoxyisopropylcarbamoyloxyphenyl]-urea, 1 and 2 kg per hectare;
IX   N-4-(p-chlorophenoxy)-phenyl-N',N-dimethylurea, 2 and 3 kg per hectare;
X   2-chloro-4-ethylamino-6-(α,α-dimethylcyanomethyl)-amino-1,3,5-triazine, 1 and 2 kg per hectare;

I + IV : 1 + 2 kg per hectare;
II + V : 1 + 1 kg per hectare;
III + VI : 1 + 2 kg per hectare;
I + VII : 1 + 2 kg per hectare;
II + VIII : 1 + 1 kg per hectare;
III + IX : 1 + 2 kg per hectare;
II + X : 1 + 1 kg per hectare.

After 4 to 5 weeks it was ascertained that the mixtures had a stronger herbicidal action than the individual active ingredients, combined with more favorable crop plant compatibility.

The results of the experiment are given in the following table:

Table

| kg/ha | I | | II | | III | | IV | | V | | VI | | VII | | VIII | | IX | | X | |
|---|---|---|---|---|---|---|---|---|---|---|---|---|---|---|---|---|---|---|---|---|
| | 1 | 3 | 1 | 2 | 1 | 3 | 2 | 3 | 1 | 2 | 2 | 3 | 2 | 3 | 1 | 2 | 2 | 3 | 1 | 2 |
| Soja hispida | 0 | 15 | 0 | 10 | 0 | 20 | 0 | 15 | 0 | 20 | 0 | 10 | 0 | 20 | 0 | 20 | 5 | 25 | 0 | 20 |
| Digitaria sanguinalis | 70 | 100 | 85 | 100 | 70 | 100 | 65 | 95 | 55 | 90 | 50 | 75 | 80 | 100 | 45 | 85 | 60 | 90 | 30 | 75 |
| Bromus tectorum | 70 | 100 | 75 | 100 | 70 | 100 | 55 | 80 | 55 | 95 | 40 | 65 | 50 | 75 | 50 | 95 | 55 | 80 | 50 | 95 |
| Amaranthus retroflexus | 15 | 50 | 25 | 50 | 15 | 50 | 60 | 85 | 70 | 100 | 70 | 95 | 90 | 100 | 50 | 95 | 45 | 90 | 45 | 85 |
| Portulaca oleracea | 15 | 50 | 25 | 55 | 20 | 55 | 60 | 85 | 70 | 95 | 65 | 90 | 95 | 100 | 65 | 100 | 60 | 95 | 70 | 100 |

| kg/ha | I + IV<br>1 + 2 | II + V<br>1 + 1 | III + VI<br>1 + 2 | I + VII<br>1 + 2 | II + VIII<br>1 + 1 | III + IX<br>1 + 2 | II + X<br>1 + 1 |
|---|---|---|---|---|---|---|---|
| Soja hispida | 0 | 0 | 0 | 0 | 0 | 0 | 0 |
| Digitaria sanguinalis | 100 | 100 | 100 | 100 | 100 | 100 | 100 |
| Bromus tectorum | 100 | 100 | 100 | 100 | 100 | 100 | 100 |
| Amaranthus retroflexus | 85 | 100 | 95 | 100 | 90 | 80 | 85 |
| Portulaca oleracea | 90 | 100 | 100 | 100 | 100 | 95 | 100 |

0 = no damage
100 = complete destruction

The action of the following mixtures corresponds to that of those above:

N-β-methoxyethyl-N-β-chloroethyl-2,6-dinitro-4-trifluoromethylaniline;
N-β-methoxyethyl-N-β-azidoethyl-2,6-dinitro-4-trifluoromethylaniline;
N-propyl-N-β-cyanoethyl-2,6-dinitro-4-trifluoromethylaniline;
N-ethyl-N-β-chloroethyl-2,6-dinitro-4-trifluoromethylaniline;
N-ethyl-N-butyl-2,6-dinitro-4-trifluoromethylaniline;
N-isobutyl-N-β-cyanoethyl-2,6-dinitro-4-trifluoromethylaniline;
N-ethyl-N-β-cyanoethyl-2,6-dinitro-4-trifluoromethylaniline;
N-methyl-N-β-cyanoethyl-2,6-dinitro-4-trifluoromethylaniline;
N-β-methoxyethyl-N-β-cyanoethyl-2,6-dinitro-4-trifluoromethylaniline;
N-butyl-N-β-cyanoethyl-2,6-dinitro-4-trifluoromethylaniline;

N-methyl-N-β-cyanoethyl-2,6-dinitro-4-trifluoromethylaniline;
N-butyl-N-β-chloropropyl-2,6-dinitro-4-trifluoromethylaniline;
N-isobutyl-N-γ-chloropropyl-2,6-dinitro-4-trifluoromethylaniline;
N-propyl-N-β-chloropropyl-2,6-dinitro-4-trifluoromethylaniline;
N-propyl-N-β-bromoethyl-2,6-dinitro-4-trifluoromethylaniline;
N,N-bis-β-(chloroethyl)-2,6-dinitro-4-trifluoromethylaniline;
N,N-bis-β-(chloroethyl)-2,6-dinitro-4-methylaniline;
N-propyl-N-allyl-4,6-dinitro-2-trifluoromethylaniline;
N-ethyl-N-β-azidoethyl-2,6-dinitro-4-trifluoromethylaniline;
N-propyl-N-β-azidoethyl-2,6-dinitro-4-trifluoromethylaniline;
N-propyl-N-β-(chloroacetyloxy)-ethyl-2,6-dinitro-4-trifluoromethylaniline;
N,N-bis-(β-chloroacetyloxy)-ethyl-2,6-dinitro-4-trifluoromethylaniline;
N-(β-chloroacetyloxy)-ethyl-2,6-dinitro-4-trifluoromethylaniline;
N-(β-methylcarbamoyloxy)-ethyl-2,6-dinitro-4-trifluoromethylaniline;
N-ethyl-N-β-bromoethyl-2,6-dinitro-4-trifluoromethylaniline;
N-β-methoxyethyl-N-β-bromoethyl-2,6-dinitro-4-trifluoromethylaniline;
N-γ-chloropropyl-N-β-chloroethyl-2,6-dinitro-4-trifluoromethylaniline;
N-propen-(1)-yl-(3)-N-β-chloroethyl-2,6-dinitro-4-methylaniline;
N-propyl-N-β-chloroethyl-2,6-dinitro-4-methylaniline;
N-propyl-N-β-azidoethyl-2,6-dinitro-4-methylaniline;
N-propyl-N-β-azidoethyl-2,6-dinitro-4-methylsulfonylaniline;
N-propyl-N-β-bromoethyl-2,6-dinitro-4-methylsulfonylaniline;
N-propyl-N-β-(chloroacetyloxy)-ethyl-2,6-dinitro-4-methylaniline;
N-propyl-N-β-(chloroacetyloxy)-propyl-2,6-dinitro-4-trifluoromethylaniline; or
N-propyl-N-β-(methylcarbamoyloxy)-propyl-2,6-dinitro-4-trifluoromethylaniline with
1-(m-tert-butylcarbamoyloxyphenyl)-3-methylurea;
1-(ethylcarbamoyloxyphenyl)-3-methylurea;
1-(m-allyl-tert-butylcarbamoyloxyphenyl)-3,3-dimethylurea;
1-(m-α,α-dimethylpropyn-(1)-yl-(3)carbamoyloxyphenyl)-3-methyl-3-methoxyurea;
1-(m-α-methyl-α-ethylpropyn(1)-yl-(3)carbamoyloxyphenyl)-3-methyl-3-methoxyurea;
1-(m-tert-butylallylcarbamoyloxyphenyl)-3-methyl-3-methoxyurea;
N-m-trifluoromethylphenyl-N'-methyl-N'-butyn-(1)yl(3)-urea;
N-3-chloro-4-methoxyphenyl-N'-methyl-N'-methoxyurea;
N-m-trifluoromethylphenyl-N-methoxymethyl-N'-methylurea;
N-m-trifluoromethylphenyl-N-methoxymethyl-N'-methyl-N'-methoxyurea;
N-m-trifluoromethylphenyl-N-acetyloxymethyl-N',N'-dimethylurea;
N-m-trifluoromethylphenyl-N-cyclohex-1-enyl-N'-methylurea;
N-3-chlorophenyl-N-cyclohex-1-enyl-N'-methylurea;
N-3-chloro-4-methoxyphenyl-N-cyclohex-1-enyl-N'-methylurea;
N-4-chlorophenyl-N-cyclohex-1-enyl-N'-methylurea;
N-phenyl-N-cyclohex-1-enyl-N'-methylurea;
N-phenyl-N-cyclohex-1-enyl-N'N'-dimethylurea;
N-4-bromophenyl-N-cyclohex-1-enyl-N'N'-dimethylurea;
N-3,4-dichlorophenyl-N-cyclohex-1-enyl-N'N'-dimethylurea;
N-3-chloro-4-methoxyphenyl-N-cyclohex-1-enyl-N'N'-dimethylurea;
N-[1- or 2- (3a,4,5,6,7,7a-hexahydro-4)-methanoindanyl]-N'N'-dimethyl-N-cyclohex-1-enylurea;
N-m-trifluoromethylphenyl-N-cyclooct-1-enyl-N'N'-dimethylurea;
N-m-trifluoromethylphenyl-N-cyclooctyl-1-enyl-N'-methylurea;
N-[5-(3a,4,5,6,7,7a-hexahydro-4)-methanoindanyl]-N'N'-dimethylurea;
N-[1- or 2-(3a,4,5,6,7,7a-hexahydro-4-)-methanoindanyl]-N'N'-dimethylurea;
N-bicyclo-(3,3,0)-octyl-N'N'-dimethylurea;
N-3,4-dichlorophenyl-N'N'-dimethylurea;
N-cyclooctyl-N'N'-dimethylurea;
N-m-dimethylcarbamoyloxyphenyl-N'-methylurea;
N-p-chlorophenyl-N-1-cyclohex-1-enyl-N'N'-dimethylurea;
N-p-fluorophenyl-N-1-cyclohex-1-enyl-N'-methylurea;
N-4-[4-methoxyphenoxyphenyl]-N'N'-dimethylurea;
N-3,4-dichlorophenyl-N'-methyl-N'-methoxyurea;
N-(3-chloro-4-bromophenyl)-N'-methyl-N'-methoxyurea;

As further examples of the synergistic action of the subject substituted anilines and substituted ureas, the following herbicidal experiments were conducted.

EXAMPLE 3

Experiment A

In the greenhouse I filled loamy sandy soil into pots and sowed it with seeds of the plants listed below. I then treated the soil prepared in this manner with the following amounts of the following individual active ingredients and mixtures thereof in the form of emulsions or dispersions:

I  N-propyl-N-β-chloroethyl-2,6-dinitro-4-trifluoromethylaniline, 0.25, 0.5, 0.75 and 1 kg per hectare II N-3-trifluoromethylphenyl-N-cyclohex-1-enyl-N',-N'-dimethylurea 0.25, 0.5, 0.75 and 1 kg per hectare III N-3,4-dichlorophenyl-N',N'-dimethylurea, 0.25, 0.5, 0.75 and 1 kg per hectare IV N-[5-(3a,4,5,6,7,7a-hexahydro-4,7-methanoindanyl)]-N',N'-dimethylurea, 0.25, 0.5, 0.75 and 1 kg per hectare V N-[1- or 2-(3a,4,5,6,7,7a-hexahydro-4,7-methanoindanyl)]-N',N'-dimethylurea, 0.25, 0.5, 0.75 and 1 kg per hectare VI N-3,4-dichlorophenyl-N'-methyl-N'-methoxyurea, 0.25, 0.5, 0.75 and 1 kg per hectare.

I + II: 0.25 + 0.75, 0.75 + 0.25, and 0.5 + 0.5 kg per hectare

I + III: 0.25 + 0.75, 0.75 + 0.25, and 0.5 + 0.5 kg per hectare

I + IV: 0.25 + 0.75, 0.75 + 0.25, and 0.5 + 0.5 kg per hectare
I + V: 0.25 + 0.75, 0.75 + 0.25, and 0.5 + 0.5 kg per hectare
I + VI: 0.25 + 0.75, 0.75 + 0.25, and 0.5 + 0.5 kg per hectare After 4 to 5 weeks it was ascertained that the mixtures had a better herbicidal action than the sum of the actions of their individual components, combined with the same good crop plant compatibility.

The results of this experiment are given below:

with the following amounts of the following individual active ingredients and mixtures thereof in the form of emulsions or dispersions:

I  N-propyl-N-(2'-chloroethyl)-2,6-dinitro-4-trifluoromethylaniline, 0.25, 0.5, 0.75 and 1.0 kg per hectare
II  N-(2-benzothiazolyl)-N-methyl-N'-methylurea, 0.25, 0.5, 0.75 and 1.0 kg per hectare
III  N-(3-chloro-4-methylphenyl)-N',N'-dimethlurea, 0.25, 0.5, 0.75 and 1.0 kg per hectare
IV  N-(3-trifluoromethylphenyl)-N',N'-dimethylurea,

Table

| Active ingredient kg/ha | I 0.25 | 0.5 | 0.75 | 1.0 | II 0.25 | 0.5 | 0.75 | 1.0 | III 0.25 | 0.5 | 0.75 | 1.0 | IV 0.25 | 0.5 | 0.75 | 1.0 |
|---|---|---|---|---|---|---|---|---|---|---|---|---|---|---|---|---|
| Crop plants | | | | | | | | | | | | | | | | |
| Gossypium hirsutum | 0 | 0 | 0 | 0 | 0 | 0 | 0 | 0 | 0 | 0 | 0 | 0 | 0 | 0 | 0 | 0 |
| Soja hispida | 0 | 0 | 0 | 0 | 0 | 0 | 0 | 0 | 0 | 0 | 0 | 0 | 0 | 0 | 0 | 0 |
| Unwanted plants | | | | | | | | | | | | | | | | |
| Digitaria sanguinalis | 25 | 45 | 60 | 85 | 20 | 35 | 50 | 60 | 24 | 40 | 54 | 65 | 25 | 45 | 55 | 70 |
| Echinochloa crus galli | 32 | 50 | 58 | 70 | 18 | 30 | 40 | 50 | 20 | 32 | 50 | 60 | 28 | 45 | 65 | 90 |
| Lamium amplexicaule | 0 | 0 | 0 | 5 | 30 | 55 | 70 | 80 | 35 | 58 | 75 | 85 | 10 | 20 | 25 | 35 |

0 = no damage
100 = complete destruction

Table

| Active ingredient kg/ha | V 0.25 | 0.5 | 0.75 | 1.0 | VI 0.25 | 0.5 | 0.75 | 1.0 | I + II 0.25 + 0.75 | 0.75 + 0.25 | 0.5 + 0.5 |
|---|---|---|---|---|---|---|---|---|---|---|---|
| Crop plants | | | | | | | | | | | |
| Gossypium hirsutum | 0 | 0 | 0 | 0 | 0 | 0 | 0 | 0 | 0 0 | 0 0 | 0 0 |
| Soja hispida | 0 | 0 | 0 | 0 | 0 | 0 | 0 | 0 | 0 0 | 0 0 | 0 0 |
| Unwanted plants | | | | | | | | | | | |
| Digitaria sanguinalis | 30 | 45 | 60 | 90 | 20 | 40 | 58 | 70 | 100 | 100 | 100 |
| Echinochloaccrus galli | 25 | 48 | 65 | 90 | 25 | 45 | 60 | 70 | 100 | 100 | 100 |
| Lamium amplexicaule | 5 | 15 | 20 | 25 | 30 | 50 | 70 | 80 | 100 | 178 | 97 |

0 = no damage
100 = complete destruction

Table

| Active ingredient kg/ha | I + III 0.25+0.75 | 0.75+0.25 | 0.5+0.5 | I + IV 0.25+0.75 | 0.75+0.75 | 0.5+0.5 | I + V 0.25+0.75 | 0.75+0.25 |
|---|---|---|---|---|---|---|---|---|
| Crop plants | | | | | | | | |
| Gossypium hirsutum | 0 | 0 | 0 | 0 | 0 | 0 | 0 | 0 |
| Soja hispida | 0 | 0 | 0 | 0 | 0 | 0 | 0 | 0 |
| Unwanted plants | | | | | | | | |
| Digitaria sanguinalis | 100 | 100 | 100 | 100 | 100 | 100 | 100 | 100 |
| Echinochloa crus galli | 100 | 100 | 100 | 100 | 100 | 100 | 100 | 100 |
| Lamium amplexicaule | 100 | 82 | 100 | 70 | 60 | 65 | 68 | 60 |

0 = no damage
100 = complete destruction

Table

| Active ingredient kg/ha | I + VI 0.25+0.75 | 0.75+0.25 | 0.5+0.5 |
|---|---|---|---|
| Crop plants | | | |
| Gossypium hirsutum | 0 | 0 | 0 |
| Soja hispida | 0 | 0 | 0 |
| Unwanted plants | | | |
| Digitaria sanguinalis | 100 | 100 | 100 |
| Echinochloa crus galli | 100 | 100 | 100 |
| Lamium amplexicaule | 100 | 80 | 95 |

0 = no damage
100 = complete destruction

EXPERIMENT B

An agricultural plot was sown with seeds of the plants listed below. The soil was then immediately treated 0.25, 0.5, 0.75 and 1.0 kg per hectare
V  N-(3-chloro-4-methoxyphenyl)-N',N'-dimethylurea, 0.25, 0.5, 0.75 and 1.0 kg per hectare
VI  N-(3-chloro-4-methoxyphenyl)-N'-methyl-N'-methoxyurea, 0.25, 0.5, 0.75 and 1.0 kg per hectare
VII  N-(3-chloro-4-methoxyphenyl)-N-cyclohex-1-enyl-N',N'-dimethylurea, 0.25, 0.5, 0.75 and 1.0 kg per hectare
VIII  N-(3-chloro-4-methylphenyl)-N-cyclohex-1-enyl-N',N'-dimethylurea, 0.25, 0.5, 0.75 and 1.0 kg per hectare.

I + II : 0.75 + 0.25, 0.5 + 0.5 and 0.25 + 0.75 kg per hectare
I + III: 0.75 + 0.25, 0.5 + 0.5 and 0.25 + 0.75 kg per hectare I + IV : 0.75 + 0.25, 0.5 + 0.5 and 0.25 + 0.75 kg per hectare
I + V : 0.75 + 0.25, 0.5 + 0.5 and 0.25 + 0.75 kg per hectare
I + VI : 0.75 + 0.25, 0.5 + 0.5 and 0.25 + 0.75 kg per hectare
I + VII: 0.75 + 0.25, 0.5 + 0.5 and 0.25 + 0.75 kg per hectare
I + VIII: 0.75 + 0.25, 0.5 + 0.5 and 0.25 + 0.75 kg per hectare After 3 to 4 weeks it was ascertained that the mixtures had a better herbicidal action than the sum of the actions of their individual components, combined with the same good crop plant compatibility.

The results of this experiment are given below:

Table

| Active ingredient kg/ha | I | | | | II | | | | III | | | | IV | | | |
|---|---|---|---|---|---|---|---|---|---|---|---|---|---|---|---|---|
| | 0.25 | 0.5 | 0.75 | 1.0 | 0.25 | 0.5 | 0.75 | 1.0 | 0.25 | 0.5 | 0.75 | 1.0 | 0.25 | 0.5 | 0.75 | 1.0 |
| Crop plants | | | | | | | | | | | | | | | | |
| Triticum aestivum | 0 | 0 | 0 | 0 | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 | 0 | 0 | 0 | 0 |
| Gossypium hirsutum | 0 | 0 | 0 | 0 | — | — | — | — | — | — | — | — | 0 | 0 | 0 | 0 |
| Unwanted plants | | | | | | | | | | | | | | | | |
| Alopecurus myosuroides | 23 | 41 | 50 | 63 | 10 | 18 | 25 | 35 | 10 | 20 | 30 | 40 | 14 | 26 | 45 | 53 |
| Stellaria media | 5 | 7 | 10 | 16 | 15 | 35 | 53 | 70 | 20 | 43 | 63 | 85 | 19 | 42 | 64 | 80 |

0 = no damage
100 = total destruction

Table

| Active ingredient kg/ha | V | | | | VI | | | | VII | | | | VIII | | | |
|---|---|---|---|---|---|---|---|---|---|---|---|---|---|---|---|---|
| | 0.25 | 0.5 | 0.75 | 1.0 | 0.25 | 0.5 | 0.75 | 1.0 | 0.25 | 0.5 | 0.75 | 1.0 | 0.25 | 0.5 | 0.75 | 1.0 |
| Crop plants | | | | | | | | | | | | | | | | |
| Triticum pestivum | 0 | 0 | 0 | 0 | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 | 0 | 0 | 0 | 0 |
| Gossypium hirsutum | — | — | — | — | — | — | — | — | — | — | — | — | — | — | — | — |
| Unwanted plants | | | | | | | | | | | | | | | | |
| Alopecurus myosuroides | 15 | 28 | 40 | 50 | 16 | 35 | 50 | 75 | 10 | 20 | 31 | 40 | 15 | 32 | 48 | 60 |
| Stellaria media | 17 | 37 | 51 | 75 | 18 | 36 | 53 | 70 | 13 | 27 | 43 | 50 | 11 | 25 | 36 | 50 |

0 = no damage
100 = complete destruction

Table

| Active ingredient kg/ha | I + II | | | I + III | | | I + IV | | |
|---|---|---|---|---|---|---|---|---|---|
| | 0.25+0.75 | 0.5+0.5 | 0.75+0.25 | 0.25+0.75 | 0.5+0.5 | 0.75+0.25 | 0.25+0.75 | 0.5+0.5 | 0.75+0.25 |
| Crop plants | | | | | | | | | |
| Triticum aestivum | 0 | 0 | 0 | 0 | 0 | 0 | 0 | 0 | 0 |
| Hordeum vulgare | 0 | 0 | 0 | 0 | 0 | 0 | 0 | 0 | 0 |
| Secale cereale | 0 | 0 | 0 | 0 | 0 | 0 | 0 | 0 | 0 |
| Gossypium hirsutum | — | — | — | — | — | — | 0 | 0 | 0 |
| Unwanted plants | | | | | | | | | |
| Alopecurus myosuroides | 78 | 88 | 90 | 85 | 95 | 91 | 96 | 100 | 95 |
| Stellaria media | 90 | 70 | 57 | 95 | 82 | 62 | 100 | 80 | 63 |

0 = no damage
100 = complete destruction

Table

| Active ingredient kg/ha | I + V | | | I + VI | | |
|---|---|---|---|---|---|---|
| | 0.25+0.75 | 0.5+0.5 | 0.75+0.25 | 0.25+0.75 | 0.5+0.5 | 0.75+0.25 |
| Crop plants | | | | | | |
| Triticum aestivum | 0 | 0 | 0 | 0 | 0 | 0 |
| Hordeum vulgare | 0 | 0 | 0 | 0 | 0 | 0 |
| Secale cereale | 0 | 0 | 0 | 0 | 0 | 0 |
| Gossypium hirsutum | — | — | — | — | — | — |
| Unwanted plants | | | | | | |
| Alopecurus myosuroides | 90 | 98 | 97 | 100 | 100 | 95 |
| Stellaria media | 88 | 75 | 60 | 90 | 75 | 60 |

0 = no damage
100 = complete destruction

Table

| Active ingredient kg/ha | I + VII | | | I + VIII | | |
|---|---|---|---|---|---|---|
| | 0.25+0.75 | 0.5+0.5 | 0.75+0.25 | 0.25+0.75 | 0.5+0.5 | 0.75+0.25 |
| Crop plants | | | | | | |
| Triticum aestivum | 0 | 0 | 0 | 0 | 0 | 0 |

Table-continued

| Active ingredient kg/ha | I + VII 0.25+0.75 | 0.5+0.5 | 0.75+0.25 | I + VIII 0.25+0.75 | 0.5+0.5 | 0.75+0.25 |
|---|---|---|---|---|---|---|
| Hordeum vulgare | 0 | 0 | 0 | 0 | 0 | 0 |
| Secale cereale | 0 | 0 | 0 | 0 | 0 | 0 |
| Gossypium hirsutum | — | — | — | — | — | — |
| Unwanted plants | | | | | | |
| Alopecurus myosuroides | 86 | 94 | 92 | 100 | 100 | 93 |
| Stellaria media | 80 | 66 | 55 | 73 | 64 | 54 |

The results of these experiments show that the mixtures have a herbicidal action far superior to the sum of the actions of their individual active ingredients.

The invention is hereby claimed as follows:

1. A herbicide composition an inert carrier containing a herbicidally effective amount of a mixture consisting essentially of
   a. N-propyl-N-β-chloroethyl-2,6-dinitro-4-trifluoromethylaniline and
   b. a member selected from the group consisting of N-3,4-dichlorophenyl-N',N'-dimethylurea, N-3,4-dichlorophenyl-N'-methyl-N'-methoxyurea, N-(3-chloro-4-methylphenyl)-N',N'-dimethylurea, N-(3-trifluoromethylphenyl)-N',N'-dimethylurea, N-(3-chloro-4-methoxyphenyl)-N',N'-dimethylurea, and N-(3-chloro-4-methoxyphenyl)-N'-methyl-N'-methoxyurea in a weight ratio of $a$ to $b$ in the range of 3:1 to 1:3.

2. A herbicide composition as claimed in claim 1 wherein compound $b$ is N-3,4-dichlorophenyl-N',N'-dimethylurea.

3. A herbicide composition as claimed in claim 1 wherein compound $b$ is N-3,4-dichlorophenyl-N'-methyl-N'-methoxyurea.

4. A herbicide composition as claimed in claim 1 wherein compound $b$ is N-(3-chloro-4-methylphenyl)-N',N'-dimethylurea.

5. A herbicide composition as claimed in claim 1 wherein compound $b$ is N-(3-trifluoromethylphenyl)-N',N'-dimethylurea.

6. A herbicide composition as claimed in claim 1 wherein compound $b$ is N-(3-chloro-4-methoxyphenyl)-N',N'-dimethylurea.

7. A herbicide composition as claimed in claim 1 wherein compound $b$ is N-(3-chloro-4-methoxyphenyl)-N'-methyl-N'-methoxyurea.

* * * * *